United States Patent
Lehmann et al.

(10) Patent No.: US 7,270,731 B2
(45) Date of Patent: Sep. 18, 2007

(54) CERMET ELECTRODES CONTAINING PLATINUM FOR THE ELECTROCHEMICAL REDUCTION OF OXYGEN

(75) Inventors: Dieter Lehmann, Stuttgart (DE); Detlef Heimann, Gerlingen (DE); Gudrun Oehler, Stuttgart (DE); Sabine Thiemann-Handler, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 749 days.

(21) Appl. No.: 10/332,832

(22) PCT Filed: Jul. 12, 2001

(86) PCT No.: PCT/DE01/02608

§ 371 (c)(1),
(2), (4) Date: Aug. 29, 2003

(87) PCT Pub. No.: WO02/04934

PCT Pub. Date: Jan. 17, 2002

(65) Prior Publication Data

US 2004/0050692 A1    Mar. 18, 2004

(30) Foreign Application Priority Data

Jul. 12, 2000    (DE) ............................... 100 33 906

(51) Int. Cl.
  *G01N 27/41*    (2006.01)
(52) U.S. Cl. ..................................... 204/424; 204/292

(58) Field of Classification Search ................ 204/424, 204/425, 290.04, 290.1, 292
See application file for complete search history.

(56) References Cited

U.S. PATENT DOCUMENTS

| | | | |
|---|---|---|---|
| 3,843,400 A | * | 10/1974 | Radford et al. ............. 429/152 |
| 4,283,441 A | | 8/1981 | Haecker et al. |
| 4,812,329 A | | 3/1989 | Isenberg et al. |
| 5,137,615 A | | 8/1992 | Friese et al. |
| 5,616,223 A | | 4/1997 | Joshi et al. |
| 5,698,267 A | * | 12/1997 | Friese et al. ............. 427/430.1 |
| 5,908,713 A | | 6/1999 | Ruka et al. |

FOREIGN PATENT DOCUMENTS

DE    3809154    12/1988

(Continued)

OTHER PUBLICATIONS

Pt-Rh Density from Platinum Metals Review, date unknown.*

(Continued)

*Primary Examiner*—Kaj K. Olsen
(74) *Attorney, Agent, or Firm*—Kenyon & Kenyon LLP

(57) ABSTRACT

Platinum metal cermet electrodes are described on which the electrochemical reduction of oxygen is made easier compared to known platinum metal cermet electrodes. The ceramic component of a platinum metal cermet electrode contains stabilized $ZrO_2$ as its main constituent, the composition of the electrode being directed toward reducing its polarization resistance.

12 Claims, 3 Drawing Sheets

FOREIGN PATENT DOCUMENTS

Figure 1:
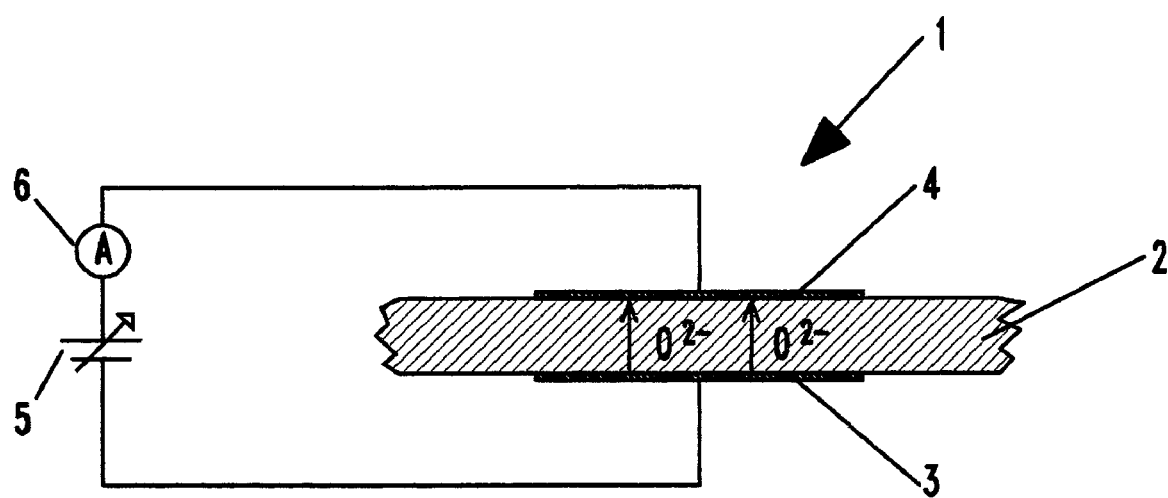

| | | |
|---|---|---|
| DE | 39 34 586 | 4/1991 |
| DE | 4217605 | 12/1992 |
| DE | 42 40 267 | 6/1994 |
| DE | 198 33 087 | 1/2000 |
| EP | 0 388 558 | 9/1990 |
| EP | 0 485 085 | 6/1999 |
| JP | 06-160332 | 6/1994 |
| WO | 00 30194 | 5/2000 |

OTHER PUBLICATIONS

Practical Handbook of Materials Science, CRC Press, p. 311, 1989.*

Pantu, P., et al., "Methane partial oxidation on Pt/CeO2-ZrO2 in the absence of gaseous oxygen", Applied Catalysis A: General, Elsevier Science, Amsterdam, NL., Bd. 193, Nr. 1-2, pp. 203-214 (Feb. 28, 2000).

* cited by examiner

CERMET ELECTRODES CONTAINING PLATINUM FOR THE ELECTROCHEMICAL REDUCTION OF OXYGEN

This application is a 371 of PCT/DE01/02608, filed on Jul. 12, 2001, which claims priority to German application 100 33 906.9, filed on Jul. 12, 2000.

BACKGROUND INFORMATION

The invention relates to platinum metal cermet electrodes for the electrochemical reduction of $O_2$, the ceramic component of which contains stabilized $ZrO_2$ as its main constituent.

The electrochemical reduction of oxygen plays a role in gas sensors for the analysis of gas mixtures containing $O_2$. Such gas sensors are described, for example, in German Patent Application 39 34 586 A1, German Patent Application 42 40 267 A1 and German Patent Application 198 33 087 A1. The platinum metal cermet electrodes used are printed on substrates of Y-stabilized $ZrO_2$. The platinum metal cermet electrodes normally have a ceramic component of 40 vol.-% (the supporting structure) and a 60 vol.-% metallic component. The supporting structure is primarily made up of Y-stabilized $ZrO_2$ which contains 10 wt.-% $Y_2O_3$ with respect to the $ZrO_2$ component in terms of order of magnitude. The ceramic addition should ensure a certain porosity of the electrode material and it should also extend the electrochemically effective three phase limit of the actual contact surface between substrate and electrode based on the ionic conductivity of the supporting structure into areas of the electrode. The $O_2$ pump flows obtained with the known electrodes are still not satisfactory.

THE INVENTION AND ITS ADVANTAGES

The object of the invention is to specify platinum metal cermet electrodes on which the electrochemical oxygen reduction is made easier compared to known platinum metal cermet electrodes.

This objective is achieved with platinum metal cermet electrodes of the type mentioned above having the features of the characterizing part of Claim 1 The polarization resistance will be defined further below.

According to an advantageous embodiment of the invention, the polarization resistance of the electrode is reduced by replacing between approximately 0.01 and approximately 1 wt.-% of the stabilized $ZrO_2$ with stabilized $CeO_2$. The substitution of a small quantity of the $ZrO_2$ with $CeO_2$ makes it possible to attain a considerable reduction of the polarization resistance and accordingly higher $O_2$ reduction flows than when standard electrodes are used.

It is even more advantageous to replace between approximately 0.02 and approximately 0.1 wt.-% of stabilized $ZrO_2$ with stabilized $CeO_2$ since the polarization resistance is then particularly low.

According to an another advantageous embodiment of the invention, it is possible to reduce the polarization resistance of the electrode by placing the metal:ceramic ratio in the electrode (in vol.-%) between approximately 65:35 and approximately 85:15 and even more preferably between 70:30 and 80:20, i.e., by increasing the metal:ceramic ratio. Apparently, when the ratio is placed into the range according to the present invention, the favorable effect of a high metallic component for a low polarization resistance and the effect of a low porosity increasing the polarization resistance (due to the relatively low ceramic component) are balanced in such a way that the polarization resistance decreases in relation to the standard ratio (60:40).

It is in fact known from the aforementioned German Patent Application 42 40 267 A1 that the metal component in Pt cermet electrodes is generally between 50 and 80 vol.-%. It is also known from German Patent Application DE 42 40 267 A1 that it is possible to use other metallic oxides such as $CeO_2$ instead of or in addition to $ZrO_2$ as ion conductors in the solid electrolyte. However, the use of the cited ranges of the metal:ceramic ratio and/or the $ZrO_2$: $CeO_2$ ratio is not known, and it is in particular not known and not suggested by the related art that it is possible to reduce the polarization resistance while maintaining the cited ranges.

It is favorable if the $CeO_2$ is stabilized using an oxide from the group $Y_2O_3$, $Gd_2O_3$, $Sc_2O3$ and $HfO_2$.

The electrodes of the present invention may be used advantageously in gas sensors for pumping off $O_2$ from test gases containing $O_2$.

Additional advantageous embodiments of the platinum metal cermet electrodes may be found in the dependent claims.

THE DRAWING

Figure 2:
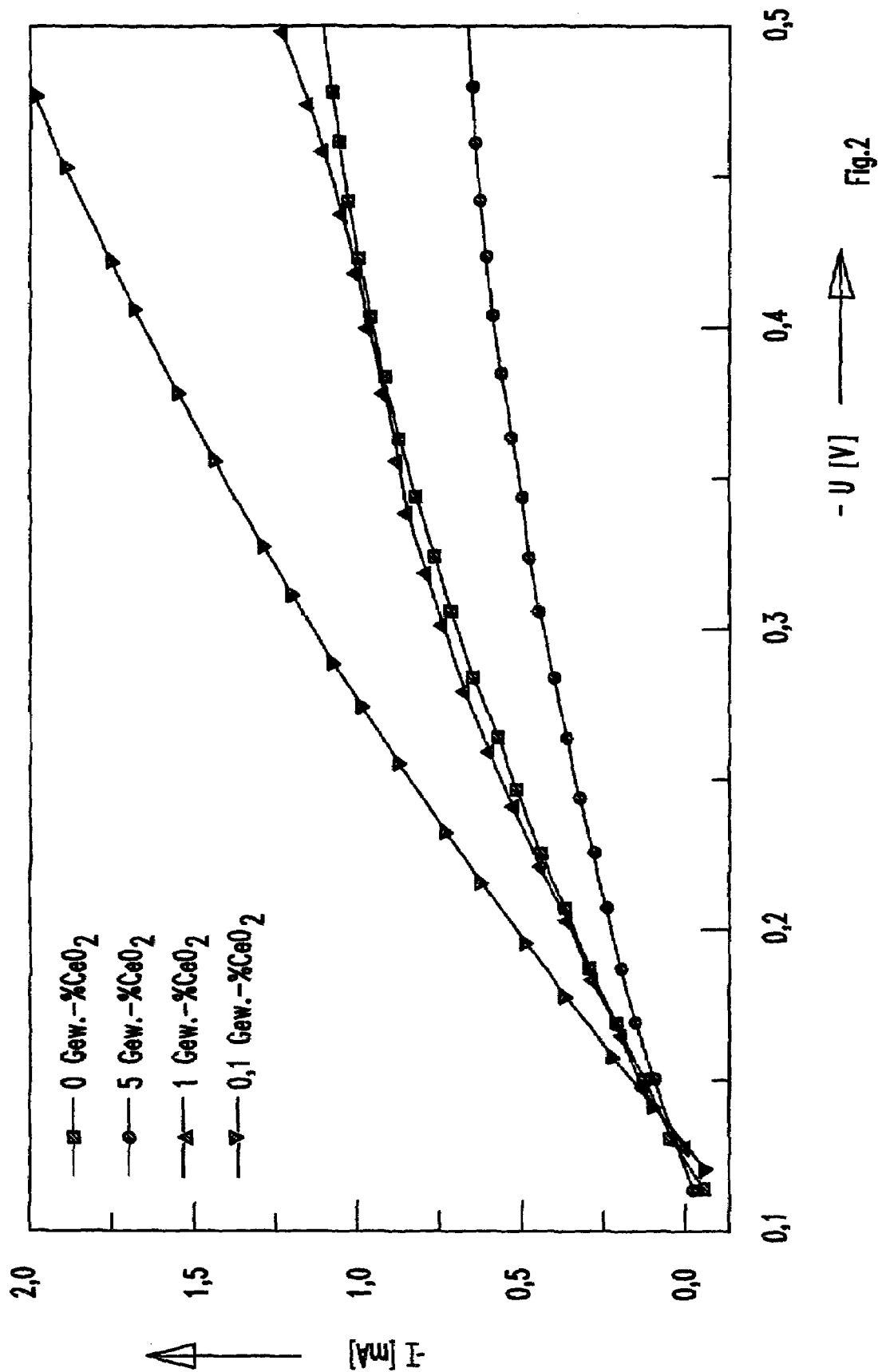
Figure 3:
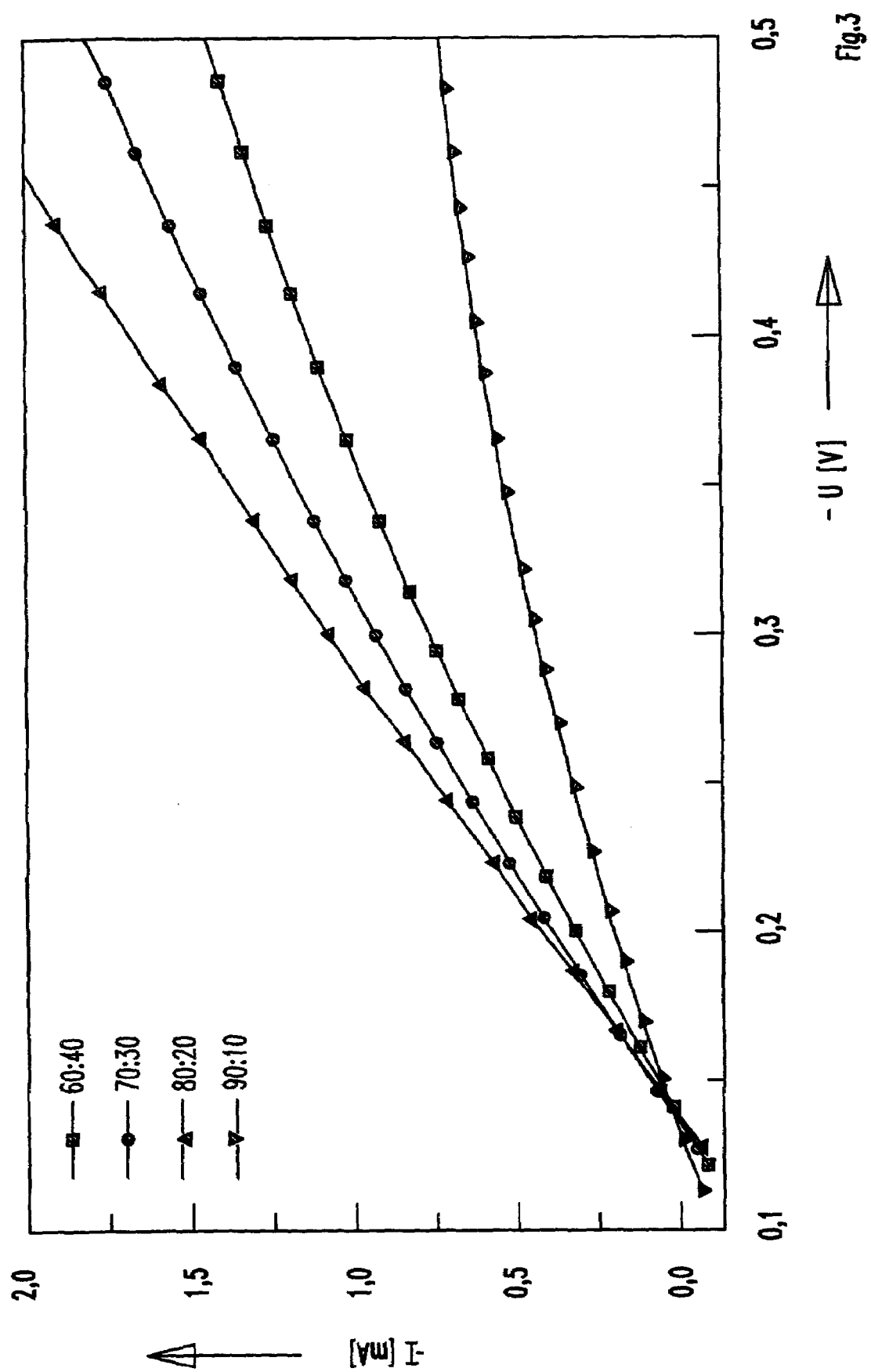

The present invention is explained in detail below with reference to exemplary embodiments illustrated by the drawing in which FIG. 1 shows a system for illustrating the invention in a schematic cross-sectional view, FIG. 2 shows a diagram in which $O_2$ reduction flows are plotted against the applied voltage for different concentrations of Y-stabilized $CeO_2$ in the ceramic matrix according to an aspect of the present invention and FIG. 3 shows a diagram in which $O_2$ reduction flows are plotted against the applied voltage for different metal:ceramic ratios according to an aspect of the present invention.

The invention will be described below primarily using the example of Pt cermet electrodes. However, it should be made clear that the invention may be used to particular advantage in conjunction with such Pt cermet electrodes and may be explained very clearly with them; however, numerous deviations from this example are possible within the context of the claims.

System 1 shown in FIG. 1 contains a thin substrate 2 made of a highly gastight solid electrolyte material having oxygen ion conductivity such as Y-stabilized $ZrO_2$, diametrically opposed Pt cermet electrodes 3 and 4 having been applied to its two surfaces. The two electrodes are electrically connected to a DC voltage source 5 in such a way that electrode 3 is the cathode and electrode 4 is the anode. An ammeter 6 is installed in one of the feeds to determine the current.

As an alternative, the metallic component in the electrodes may be made up of another precious metal from the eighth subgroup of the periodic system of the elements or of mixtures of such elements such as Pt/Rh, Pt/Ir or Pt/Pd. In order to demonstrate the invention, different proportions of the Y-stabilized $ZrO_2$ were replaced by stabilized $CeO_2$ at least in the electrode connected as the cathode in a series of tests and the metal:ceramic ratio was varied in another series of tests.

If a gas stream containing $O_2$ is directed past the heated system shown in FIG. 1, $O_2$ is electrochemically reduced at the electrode connected as the cathode when the electrodes are energized and a corresponding $O_{2-}$ stream flows between the electrodes. One measure of the reduction activity of the electrode is the polarization resistance (Rp). The Rp is a variable calculated from the initial slope of the cathodic I/U characteristic, which is a measure of the resistance that the electrode puts up to the $O_2$ reduction. The Rp should be as low as possible.

The inventors have determined that the polarization resistance is reduced in relation to that determined for standard electrodes if a specific quantity of the Y-stabilized $ZrO_2$ is replaced by Y-stabilized $CeO_2$ corresponding to the formula $Ce_{0.84}Y_{0.16}O_{1.92}$. The cathodic I/U characteristics in FIG. 2 show that if approximately 0.1 wt.-% Y-stabilized $ZrO_2$ is replaced by Y-stabilized $CeO_2$ (molar ratio of Y-stab. $ZrO_2$:Y-stab. $CeO_2$=0.999:0.0008), the polarization resistance is lower than if 1 or 5 wt.-% Y-stabilized $ZrO_2$ is replaced by Y-stabilized $CeO_2$ (molar ratio of Y-stab. $ZrO_2$:Y-stab. $CeO_2$=0.99:0.0084 or Y-stab. $ZrO_2$:Y-stab. $CeO_2$=0.959:0.0405) or if the $ZrO_2$ contains no $CeO_2$. The characteristics are based on measured data that was obtained on system 1 (see FIG. 1) heated to approximately 700° C. with a test gas containing $N_2$ and 500 ppm $O_2$ flowing past.

Similar results are obtainable if the $CeO_2$ is stabilized using an oxide from the group $Sc_2O_3$, $Gd_2O_3$ and $HfO_2$ instead of with $Y_2O_3$. If $Gd_2O_3$ is used, the composition of the stabilized $CeO_2$ advantageously corresponds to the formula $Ce_{0.8}Gd_{0.2}O_{1.9}$.

The inventors were also able to show that it is also possible to influence the polarization resistance by varying the metal:ceramic ratio in the electrodes (at least in electrode 3 connected as a cathode). The cathodic I/U characteristics in FIG. 3 substantiate that the polarization resistance is lower if the metal:ceramic ratio is in the range between approximately 70:30 arid approximately 80:20 than if the ratio corresponds to the standard value (60:40) or is clearly above 80:20. The characteristics are based on measured data which was obtained on system 1 heated to approximately 700° C. (see FIG. 1) with a test gas containing $N_2$ and 500 ppm $O_2$ flowing past.

The calculated polarization resistances were at the values indicated in the table:

TABLE

| Metal:ceramic ratio (vol.-%) | Rp (Ω) |
|---|---|
| 60:40 (standard) | 83.7 |
| 70:30 | 55.3 |
| 80:20 | 50.6 |
| 90:10 | 221.5 |

In order to produce standard Pt cermet electrodes applied to a solid electrolyte substrate, an initial stage of the solid electrolyte body formed from $ZrO_2$, stabilized $Y_2O_3$ and customary additives and a suspension are prepared, which in a proportion by volume of 60:40 contains Pt powder and a correspondingly fine-particle preformed ceramic precursor of a raw material mixture of fixed weight quantities of $ZrO_2$ and $Y_2O_3$ and if necessary a small quantity of—for example—$Al_2O_3$, the ceramic components being mixed into a paste with the Pt powder. The unsintered solid electrolyte body is then impressed with the paste at a layer thickness of 10 to 30 μm followed by drying and finally the paste and the solid electrolyte substrate are sintered together into a solid at between approximately 1300 and approximately 1600° C.

If electrodes are to be produced that differ from the standard electrodes by only a greater metal:ceramic ratio, apart from using relatively larger Pt powder quantities, it is possible to proceed just as described above.

If electrodes are to be produced, with one part of the Y-stabilized $ZrO_2$ being replaced by Y- or Gd-stabilized $CeO_2$, a Ce salt and a Y salt or a Gd salt are precipitated together in the correct proportion, dried, calcined and the fixed quantity is then added to the raw material mixture containing $Y_2O_3$ and $ZrO_2$. Apart from these additional processing steps, the production method is carried out as described above.

System 1 shown in FIG. 1 is advantageously used in a gas sensor to analyze gas mixtures containing $O_2$ as part of a pump cell for pumping off $O_2$ from the test gases, at least the cathode being designed according to the present invention.

What is claimed is:

1. A platinum metal cermet electrode for an electrochemical reduction of oxygen, comprising:
    a ceramic component including stabilized $ZrO_2$, wherein:
        the cermet electrode includes a metal:ceramic ratio (in vol.-%) between 70:30 and 80:20 to reduce a polarization; and
        between approximately 0.01 and approximately 1 wt.-% of the stabilized $ZrO_2$ is replaced by stabilized $CeO_2$.

2. The cermet electrode as recited in claim 1, wherein:
    between approximately 0.02 and approximately 0.1 wt.-% of stabilized $ZrO_2$ is replaced by stabilized $CeO_2$.

3. The cermet electrode as recited in claim 2, wherein:
    the stabilized $CeO_2$ is stabilized using an oxide from the group $Y_2O_3$, $Gd_2 O_3$, $Sc_2 O_3$ and $HfO_2$.

4. The cermet electrode as recited in claim 2, wherein:
    a composition of the stabilized $CeO_2$ is stabilized using an oxide of a trivalent metal that roughly corresponds to the formula $Ce_{0.8}Me'''_{0.2}O_{1.9}$.

5. The cermet electrode as recited in claim 4, wherein:
    the composition of the stabilized $CeO_2$ is stabilized using $Gd_2O_3$ corresponding to the formula $Ce_{0.8}Gd_{0.2}O_{1.9}$.

6. The cermet electrode as recited in claim 4, wherein:
    the composition of the stabilized $CeO_2$ is stabilized using $Y_2O_3$ corresponding to the formula $Ce_{0.775}Y_{0.225}O_{1.88}$.

7. The cermet electrode as recited in claim 1, wherein:
    the $ZrO_2$ is stabilized using $Y_2O_3$.

8. The cermet electrode as recited in claim 7, wherein:
    approximately 8 to approximately 15 wt.-% $Y_2O_3$ is present with respect to a quantity of the $ZrO_2$.

9. The cermet electrode as recited in claim 1, further comprising:
    a structure including a platinum metal that includes at least one metal from the group Pt, Rh, Ir, and Pd.

10. The cermet electrode as recited in claim 9, wherein:
    a metallic component of the cermet electrode is selected from one of a metal and a metal alloy from the group Pt, Pt/Rh, Pt/Ir and Pt/Pd.

11. An $O_2$-reducing system connectable to a voltage source, comprising:
    a solid electrolyte substrate including stabilized $ZrO_2$ and a plurality of platinum metal cermet electrodes applied to both sides of the solid electrolyte substrate, each cermet electrode including:
        a ceramic component including stabilized $ZrO_2$, wherein the cermet electrode includes a metal:ceramic ratio (in vol.-%) between 70:30 and 80:20 to reduce a polarization resistance, and between approximately 0.01 and approximately 1 wt.-% of the stabilized $ZrO_2$ is replaced by stabilized $CeO_2$.

12. The $O_2$-reducing system as recited in claim 11, wherein:
    at least one cermet electrode forms a cathode.

* * * * *